US012779109B2

(12) United States Patent
Lee et al.

(10) Patent No.: US 12,779,109 B2
(45) Date of Patent: Nov. 3, 2026

(54) INJECTION PREPARATION KIT AND INJECTION PREPARATION SYSTEM COMPRISING SAME

(71) Applicant: MEINNTECH CO., LTD., Anyang-si (KR)

(72) Inventors: Kun Hyung Lee, Seoul (KR); Sang Bin Lee, Seoul (KR); Ji Eun Lee, Seoul (KR)

(73) Assignee: MEINNTECH CO., LTD., Anyang-si (KR)

( * ) Notice: Subject to any disclaimer, the term of this patent is extended or adjusted under 35 U.S.C. 154(b) by 930 days.

(21) Appl. No.: 17/925,091

(22) PCT Filed: Nov. 9, 2020

(86) PCT No.: PCT/KR2020/015626
§ 371 (c)(1),
(2) Date: Nov. 14, 2022

(87) PCT Pub. No.: WO2021/230445
PCT Pub. Date: Nov. 18, 2021

(65) Prior Publication Data

US 2023/0233754 A1 Jul. 27, 2023

(30) Foreign Application Priority Data

May 13, 2020 (KR) ........................ 10-2020-0056969

(51) Int. Cl.
*A61M 39/22* (2006.01)
*A61J 1/14* (2023.01)
*A61M 5/14* (2006.01)

(52) U.S. Cl.
CPC .................. *A61M 5/14* (2013.01); *A61J 1/14* (2013.01); *A61M 39/223* (2013.01)

(58) Field of Classification Search
CPC ...... A61J 1/065; A61J 1/10; A61J 1/14; A61J 1/2062; A61J 1/2089; A61J 3/002;
(Continued)

(56) References Cited

U.S. PATENT DOCUMENTS 4,710,166 A * 12/1987 Thompson ............ A61M 5/172 604/65
2001/0010238 A1 8/2001 Bynum
(Continued)

FOREIGN PATENT DOCUMENTS

CN 105396198 A 3/2016
JP 2013-516268 A 5/2013
(Continued)

OTHER PUBLICATIONS

Search Report, mailed Feb. 25, 2021, for International Application No. PCT/KR2020/015626.
(Continued)

*Primary Examiner* — Kai H Weng
(74) *Attorney, Agent, or Firm* — LRK PATENT LAW FIRM

(57) ABSTRACT

Disclosed is an intravenous drug dispensing kit including: a cylinder cartridge for introducing and discharging external fluids through changes in the volume of a cylinder occurring when a pair of first and second pistons disposed therein is fixed and rotates relatively to each other; a first tube connected to an outlet tube of the cylinder cartridge; a three-way valve having a first introducing flow path, a second introducing flow path, and a discharge flow path connected to any one of the first introducing flow path and the second introducing flow path; a second tube for connecting the discharge flow path of the three-way valve to an inlet tube of the cylinder cartridge; a third tube connected to the first introducing flow path of the three-way valve; and a fourth tube
(Continued)

connected to the second introducing flow path of the three-way valve.

21 Claims, 14 Drawing Sheets

(58) Field of Classification Search
CPC .......... A61M 2039/0027; A61M 39/10; A61M 39/223; A61M 5/14; A61M 5/1407; A61M 5/14212; A61M 5/1422; A61M 5/14236; A61M 5/16827
See application file for complete search history.

(56) References Cited

U.S. PATENT DOCUMENTS

| | | | | |
|---|---|---|---|---|
| 2005/0234407 | A1* | 10/2005 | Spohn | A61M 39/10 604/122 |
| 2007/0156089 | A1* | 7/2007 | Yu | A61M 5/16827 604/131 |
| 2015/0029816 | A1 | 1/2015 | Beyer et al. | |

FOREIGN PATENT DOCUMENTS

| | | | | |
|---|---|---|---|---|
| JP | 2019-511980 | A | 5/2019 | |
| KR | 10-1998-0021443 | A | 6/1998 | |
| KR | 10-0948632 | B1 | 3/2010 | |
| KR | 10-2019-0111513 | A | 10/2019 | |
| KR | 10-2172525 | B1 | 10/2020 | |
| WO | 2013-099946 | A1 | 7/2013 | |
| WO | WO-2015020374 | A1 * | 2/2015 | A61M 5/1422 |
| WO | 2020/088960 | A2 | 5/2020 | |
| WO | 2020/088960 | A3 | 5/2020 | |

OTHER PUBLICATIONS

Written Opinion, mailed Feb. 25, 2021, for International Application No. PCT/KR2020/015626.
CNIPA Office Action, dated Sep. 3, 2024, for Chinese Patent Application No. 202080101988.4 which corresponds to the above-identified U.S. application.
JPO Office Action, dated Oct. 31, 2023 for Japanese Patent Application No. 2022-569626 which corresponds to the above-identified U.S. application.
European Search Report, mailed Apr. 25, 2024, for International Application No. PCT/KR2020015626.

* cited by examiner

INJECTION PREPARATION KIT AND INJECTION PREPARATION SYSTEM COMPRISING SAME

CROSS-REFERENCE TO RELATED APPLICATIONS

The present application is a U.S. National Phase entry from International Application No. PCT/KR2020/015626, filed on Nov. 9, 2020, which claims priority to Korean Patent Application No. 10-2020-0056969, filed on May 13, 2020, the disclosure of which is incorporated by reference herein in their entirety.

TECHNICAL FIELD

The present invention relates to an intravenous drug dispensing kit and an intravenous drug dispensing system having the same, and more specifically, to an intravenous drug dispensing kit and an intravenous drug dispensing system having the same that are capable of having a closed system for minimizing risk of contamination from external environments, while reducing a working amount and mistake of a worker, so that an intravenous drug is dispensed and administered to a patient in a safe and accurate manner.

BACKGROUND ART

In the case where blood transfusion is needed to treat excessive bleeding occurring a disease, an accident, or an operation in a medical site, in the case of a disease with infection or weak immunity, or in the case of a body lacks water, electrolyte, or nutrients, generally, blood, a ringer solution, an amino acid liquid, or a medical liquid as one of a replacement therapy, deficiency correction, and a treatment therapy is infused into a patient's body.

To inject an intravenous drug such as blood, a medicine, and the like (hereinafter, referred to simply as "intravenous drug") with an accurate amount and at an accurate flow rate as prescribed by a doctor into the patient's body, a syringe pump, an infusion pump, and the like are used. The syringe pump is configured to push a plunger of a syringe to apply a pressure to an intravenous drug inside the syringe so that the intravenous drug is infused into the patient's body, and the infusion pump is configured to allow an infusion tube of a medical liquid container hung to a height where appropriate gravity is applied to the patient to be pressurized to inject the intravenous drug to the patient's body. That is, the syringe pump and the infusion pump are distinguishedly used according to the shapes and types of containers in which the intravenous drug is sterilized and sealed, and the operation for pushing the plunger in the syringe pump and the operation for repeatedly pressurizing the infusion tube in the infusion pump are accurately performed by the control of motors, so that infusion amounts, speeds, and time can be kept as prescribed by the doctor.

That is, toxic medicines such as an anticancer agent and a contrast agent may be generally contained in the intravenous drug. The anticancer agent has to be treated by a pharmacy specialist in an aseptic dispensing chamber, and before the pharmacy specialist enters the aseptic dispensing chamber, accordingly, he or she washes his or her hands and wears his or her personal protective equipment such as antibacterial clothing, antibacterial shoes, a mask, a hair cap, protection gloves, protection glasses, and the like. Further, surrounding environments including work stands even in the aseptic dispensing chamber have to be disinfected, the drugs of the prescription have to be accurately checked, and a syringe, a needle, an ampoule, and the like have to be disinfected and then thrown away in determined methods after the use. Also, the dispensed intravenous drug in the aseptic dispensing chamber has to be kept to a sterilized state, and just before the intravenous drug is infused into the patient's body, it is released from the sealed state, thereby minimizing risk of contamination.

Like this, the processes of treating the toxic medicines such as an anticancer agent are very complicated and strict, and even in the case of a high-skilled pharmacy specialist, it is always difficult and dangerous when he or she directly treats the toxic medicines. Further, if a plurality of toxic medicines is mixedly introduced into a single pack, the complicate processes have to be repeatedly carried out, and in this case, there is a high possibility that errors or mistakes in an amount of medicine administered may occur. In specific, it is not easy for the pharmacy specialist wearing his or her personal protective equipment to keep his or her concentration for long hours, and therefore, if he or she is responsible for the dispensing of the intravenous drug, an excessive load may be applied to him or her.

So as to solve such problems in conventional practices, an automatic dispensing robot for dispensing an intravenous drug having cytotoxicity has been introduced. The automatic dispensing robot is configured to have multi-joint robot arms disposed in an internal space where an aseptic environment is kept to extract a specific medicine sorted by barcode scanning, based on the prescription, with a syringe and to introduce the extracted medicine into a medical liquid container to be dispensed in an automated manner. That is, the multi-joint robot arms serve as the pharmacy specialist in the conventional practices.

However, the automatic dispensing robot is very expensive when compared to its operation ratio, and accordingly, only several robots are sold to large hospitals with capital power as main customers, so that it is obvious that they may not prevail in generally medical sites where hundreds of thousands of anticancer agents per year are dispensed.

PRIOR ART LITERATURE

Patent Document (Patent document 1) Korean Patent No. 10-0948632 (Dated Mar. 12, 2010)

DISCLOSURE OF THE INVENTION

Technical Problems

Accordingly, it is an object of the present invention to provide an intravenous drug dispensing kit and an intravenous drug dispensing system having the same that are capable of performing dispensing of all types of drugs, particularly performing dispensing of intravenous drugs in which toxic anticancer agent or a contrast agent is contained so that it can be carefully managed in strict and limited conditions, in safe, sanitary, and convenient manners, at a low cost.

Technical Solutions

To accomplish the above-mentioned objects, according to one aspect of the present invention, an intravenous drug dispensing kit may include: a cylinder cartridge for introducing and discharging external fluids through changes in the volume of a cylinder occurring when a pair of first and second pistons disposed therein is fixed and rotates relatively to each other; a first tube connected to an outlet tube of the cylinder cartridge; a three-way valve for connecting any one of a first introducing flow path and a second introducing flow path to a discharge flow path; a second tube for connecting the discharge flow path of the three-way valve to an inlet tube of the cylinder cartridge; a third tube connected to the first introducing flow path of the three-way valve; and a fourth tube connected to the second introducing flow path of the three-way valve.

In this case, the first tube and the third tube are connected to an infusion pack, and the fourth tube is connected to a medical liquid container.

Further, the fourth tube and the medical liquid container are connected to each other by means of an adapter having an air introducing function.

The intravenous drug dispensing kit may further include at least one or more additional three-way valves, each additional three-way valve having a first introducing flow path and a discharge flow path connected to any one of the second tube, the third tube, and the fourth tube, and in this case, the additional three-way valve has a second introducing flow path connected to an additional medical liquid container.

Otherwise, the additional three-way valve may have a second introducing flow path connected to the infusion pack, the first tube and the third tube are connected to an empty infusion pack, and the fourth tube is connected to the medical liquid container.

Further, the cylinder cartridge may include an upper rotation member and a lower rotation member freely rotating with respect each other, while forming a circular cylinder space between the upper rotation member and the lower rotation member, and the first piston may be coupled to the upper rotation member to rotate along the cylinder space, while the second piston may be coupled to the lower rotation member to rotate along the cylinder space.

To accomplish the above-mentioned objects, according to another aspect of the present invention, an intravenous drug dispensing system may include the intravenous drug dispensing kit; and a cylinder pump for mounting the cylinder cartridge of the intravenous drug dispensing kit thereon to drive the pair of first and second pistons disposed inside the cylinder cartridge independently of each other.

The cylinder pump may include a cylinder driving part for driving the pair of first and second pistons disposed inside the cylinder cartridge independently of each other and a controller for controlling the cylinder driving part, and the controller controls amounts and flow rates of the liquid introduced and discharged through the cylinder cartridge, with preset values.

Further, the controller of the cylinder pump may control the cylinder driving part to allow the medical liquid of the medical liquid container connected to the fourth tube to be introduced by the preset amount and then discharged to the infusion pack connected to the first tube.

In this case, on the three-way valve, the second introducing flow path connected to the fourth tube and the discharge flow path connected to the second tube are open.

Further, the cylinder driving part may include a first driving part for operating the upper rotation member of the cylinder cartridge and a second driving part for operating the lower rotation member of the cylinder cartridge, the cylinder driving part having a structure of a double shaft in which a second driving shaft of the second driving part is inserted into a first driving shaft of the first driving part.

According to an embodiment of the present invention, the first driving part and the second driving part may have worm gear structures.

To accomplish the above-mentioned objects, according to yet another aspect of the present invention, an intravenous drug dispensing method may include: a first step of preparing the intravenous drug dispensing kit, connecting the infusion pack to the first tube and the third tube, and connecting the medical liquid container to the fourth tube; a second step of mounting the cylinder cartridge of the intravenous drug dispensing kit onto a cylinder pump for driving the pair of first and second pistons disposed inside the cylinder cartridge independently of each other; a third step of inputting an amount of the medical liquid in the medical liquid container to be introduced into the infusion pack to the cylinder pump; a fourth step of opening the second introducing flow path connected to the fourth tube and the discharge flow path connected to the second tube, on the three-way valve; and a fifth step of operating the cylinder pump to introduce the medical liquid in the medical liquid container into the infusion pack by the set amount.

After the fifth step, to form a circulation flow path of a fluid in the infusion pack by the operation of the three-way valve, the first introducing flow path connected to the third tube and the discharge flow path connected to the second tube are open on the three-way valve, and the cylinder pump operates to circulate the fluid in the infusion pack through the cylinder cartridge, so that the medical liquid remaining in the tubes is completely introduced into the infusion pack.

Between the third step and the fourth step, the intravenous drug dispensing method may include a priming step of removing air from the first to third tubes, the priming step being performed to open the first introducing flow path connected to the third tube and the discharge flow path connected to the second tube on the three-way valve and to circulate the fluid in the infusion pack through the cylinder cartridge, so that the air inside the first to third tubes is removed.

According to embodiments of the present invention, the intravenous drug dispensing method may further include, after the medical liquid container is replaced with an additional medical liquid container, a step of operating the cylinder pump to introduce the medical liquid in the additional medical liquid container into the infusion pack by a set amount.

Otherwise, the first step may include a step of connecting a first introducing flow path and a discharge flow path of at least one additional three-way valve to any one of the second to fourth tubes and connecting the additional medical liquid container to a second introducing flow path of the additional three-way valve, and the intravenous drug dispensing method may further include, after the fifth step, a mixing step of closing the discharge flow path to the medical liquid container, opening the discharge flow path to the additional medical liquid container, and operating the cylinder pump to introduce the medical liquid in the additional medical liquid container into the infusion pack by the set amount.

Meanwhile, the first step may include a step of connecting an empty infusion pack to the first tube and the third tube, connecting a first introducing flow path and the discharge flow path of the at least one additional three-way valve to any one of the second to fourth tubes, and connecting the infusion pack to a second introducing flow path of any one additional three-way valve, and the third to fifth steps may be carried out by introducing the fluid in the infusion pack connected to the second introducing flow path of the additional three-way valve into the empty infusion pack by the set amount, closing the discharge flow path to the infusion pack, opening the discharge flow path to the medical liquid container, and introducing the medical liquid in the medical liquid container into the empty infusion pack by the set amount.

The intravenous drug dispensing method may further include, after the fifth step, a finishing step of removing the medical liquid container and the fourth tube from the cylinder cartridge and closing the second introducing flow path of the three-way valve, and otherwise, a finishing step of removing the medical liquid container, the fourth tube, and the second tube from the cylinder cartridge and connecting the third tube to the inlet tube.

To accomplish the above-mentioned objects, according to still another aspect of the present invention, an intravenous drug dispensing kit, which is used to dissolve a powdered medicine, may include: a first tube connected to an outlet tube of the cylinder cartridge; a powdered medicine container connected to the first tube; a second tube connected to an inlet tube of the cylinder cartridge; and a diluent pack connected to the second tube.

To accomplish the above-mentioned objects, according to yet still another aspect of the present invention, an intravenous drug dispensing method may include: a first step of preparing the intravenous drug dispensing kit; a second step of mounting the cylinder cartridge of the intravenous drug dispensing kit onto a cylinder pump for driving the pair of first and second pistons disposed inside the cylinder cartridge independently of each other; a third step of inputting an amount of a diluent in the diluent pack to be introduced into a powdered medicine container to the cylinder pump; and a fourth step of operating the cylinder pump to introduce the diluent in the diluent pack into the powdered medicine container by the set amount.

Advantageous Effects

According to the present invention, if the intravenous drug dispensing kit is used, the cylinder pump performs suction and discharge together so that the conventional work with the syringe is automatically achieved to reduce the labors needed, thereby greatly suppressing risk occurring when toxic medical liquids are treated, automatically performing accurate metering, and removing worrying about errors upon the dispensing.

Further, in the process of dispensing the intravenous drug in the conventional practices, contamination or infection may occur because the intravenous drug is exposed to external environments, but according to the present invention, while the intravenous drug dispensing kit is kept to the closed system, all dispensing processes are performed, so that the conventional processes of inserting and drawing a needle are not needed, thereby advantageously removing risk of contamination of the infusion pack.

BEST MODE FOR INVENTION

Figure 1:
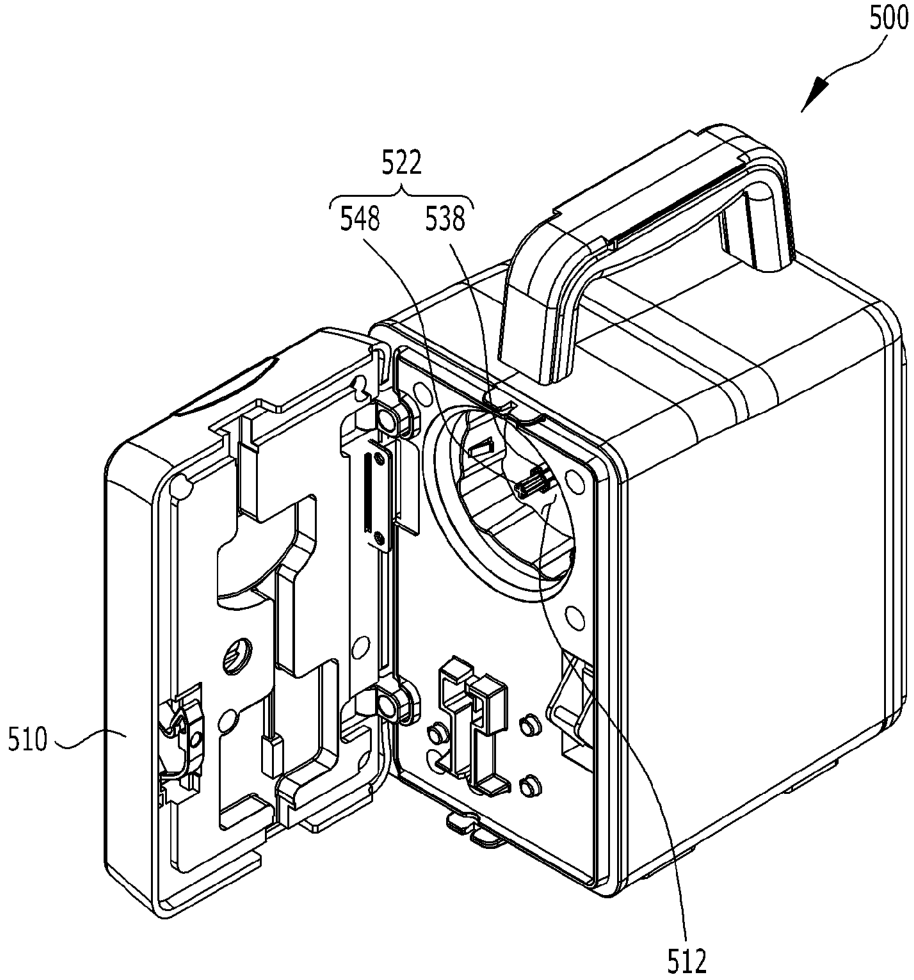
FIG. 1 is a perspective view showing a conventional cylinder pump issued to the same applicant as the invention.

The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention.

Terms used in this application are used to only describe specific exemplary embodiments and are not intended to restrict the present invention. An expression referencing a singular value additionally refers to a corresponding expression of the plural number, unless explicitly limited otherwise by the context. In this application, terms, such as "comprise", "include", or 'have", are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, or parts, or combinations thereof.

Hereinafter, embodiments of the present invention will be described in detail with reference to the attached drawings wherein the corresponding parts in the embodiments of the present invention are indicated by corresponding reference numerals and the repeated explanation on the corresponding parts will be avoided. If it is determined that the detailed explanation on the well known technology related to the present invention makes the scope of the present invention not clear, the explanation will be avoided for the brevity of the description. In the description, some of the components shown in the drawing may be magnified, omitted, or schematically suggested.

The present invention relates to an intravenous drug dispensing kit 10 and an intravenous drug dispensing system 1000 having the same, and in specific, the intravenous drug dispensing kit 10 has a closed system for minimizing risk of contamination from external environments, while reducing a working amount and mistake of a worker, so that an intravenous drug is dispensed in a safe and accurate manner and after that, the dispensed intravenous drug of the intravenous drug dispensing kit 10 is directly administered to a patient's body. In this case, to explain the intravenous drug dispensing kit 10 of the present invention, there is a need to describe a cylinder pump 500 as the prior art patent issued to the same applicant as the invention. However, a configuration of the cylinder pump 500 will be briefly explained to an extent required to understand the present invention.

Figure 2:
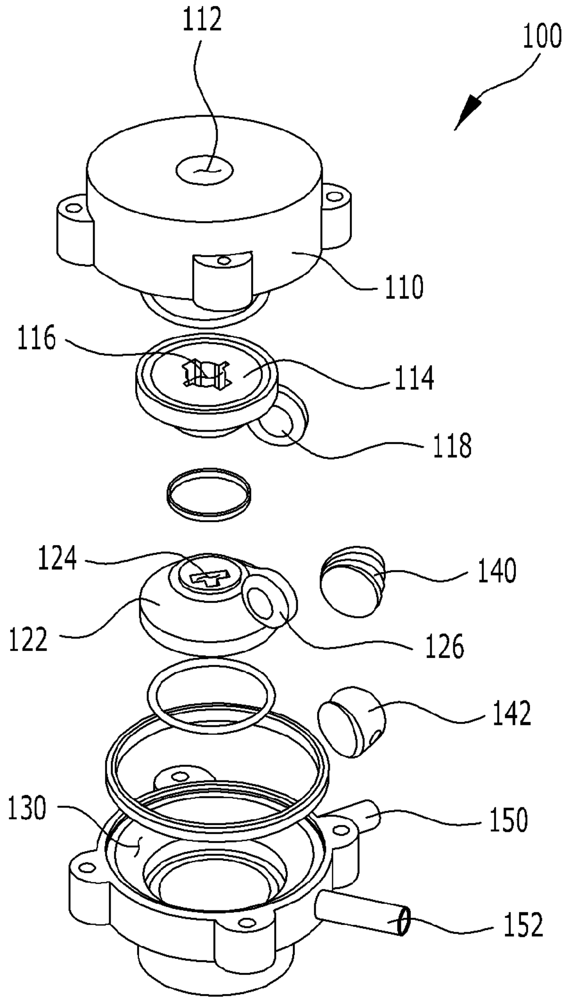
FIG. 2 is an exploded perspective view showing a cylinder cartridge coupled to the cylinder pump of FIG. 1.

FIG. 1 shows the outer appearance of the cylinder pump 500 issued to the same applicant as the invention, and in this case, a front cover 510 of the cylinder pump 500 is open. If the front cover 510 is open, the cylinder pump 500 couples a cylinder cartridge 100 as shown in FIG. 2 thereto, and FIG. 3*b* shows a state where the cylinder cartridge 100 is coupled to the interior of the cylinder pump 500. In this case, the cylinder cartridge 100 is automatically locked onto the cylinder pump 500 so that the cylinder cartridge 100 coupled to a driving shaft 522 is fixed to the cylinder pump 500, without any movement, while operating. Hereinafter, explanations of the cylinder cartridge 100, a cylinder driving part 520, and their operating principle will be given.

Referring to FIG. 2, the cylinder cartridge 100 includes an upper housing 110 and a lower housing 120 sealedly coupled to each other to provide a single housing, and an upper rotation member 114 and a lower rotation member 122 are disposed aligned coaxially inside the upper housing 110 and the lower housing 120 and thus rotate independently of each other. Further, the upper rotation member 114 and the lower rotation member 122 have the shapes of conical stands, and thus, they are arranged to allow peaks (extending from generating lines) of the conical stands to face to each other, so that a single concave space is formed between the upper housing 110 and the lower housing 120. The circular space is used as a cylinder space 130.

The upper rotation member 114 and the lower rotation member 122 have an upper fastening member 118 and a lower fastening member 126 formed integrally on the slope surfaces thereof, so that a first piston 140 is coupled to the upper fastening member 118, and a second piston 142 is coupled to the lower fastening member 126. The first piston 140 and the second piston 142 are made of an elastic material that is changed in shape to come into close contact with a surrounding surface, like a rubber packing coupled to a plunger of a general syringe. That is, the first piston 140 and the second piston 142 come into close contact with the inner peripheral surfaces of the housings, and as the first piston 140 or the second piston 142 rotates, a partially negative pressure or a partially positive pressure is formed in the circular cylinder space 130. A circular member having no reference numeral in FIG. 2 represents a sealing member.

Further, the lower housing 120 includes an inlet tube 150 and an outlet tube 152, and infusion tubes are fitted to the inlet tube 150 and the outlet tube 152. Further, the upper housing 110 has a driving shaft insertion hole 112 formed at the center thereof, and on the coaxial line with the driving shaft insertion hole 112, the upper rotation member 114 has a first driving shaft fastening hole 116 formed thereon, while the lower rotation member 122 has a second driving shaft fastening hole 124 formed thereon. In this case, the first driving shaft fastening hole 116 is larger than the second driving shaft fastening hole 124. That is, an approach to the second driving shaft fastening hole 124 through the first driving shaft fastening hole 116 is possible. Further, the first driving shaft fastening hole 116 and the second driving shaft fastening hole 124 have shapes with given directionality. In the embodiment as shown, the first driving shaft fastening hole 116 has the shape of a cross having different widths, and the second driving shaft fastening hole 124 has the shape of T.

Figure 3:
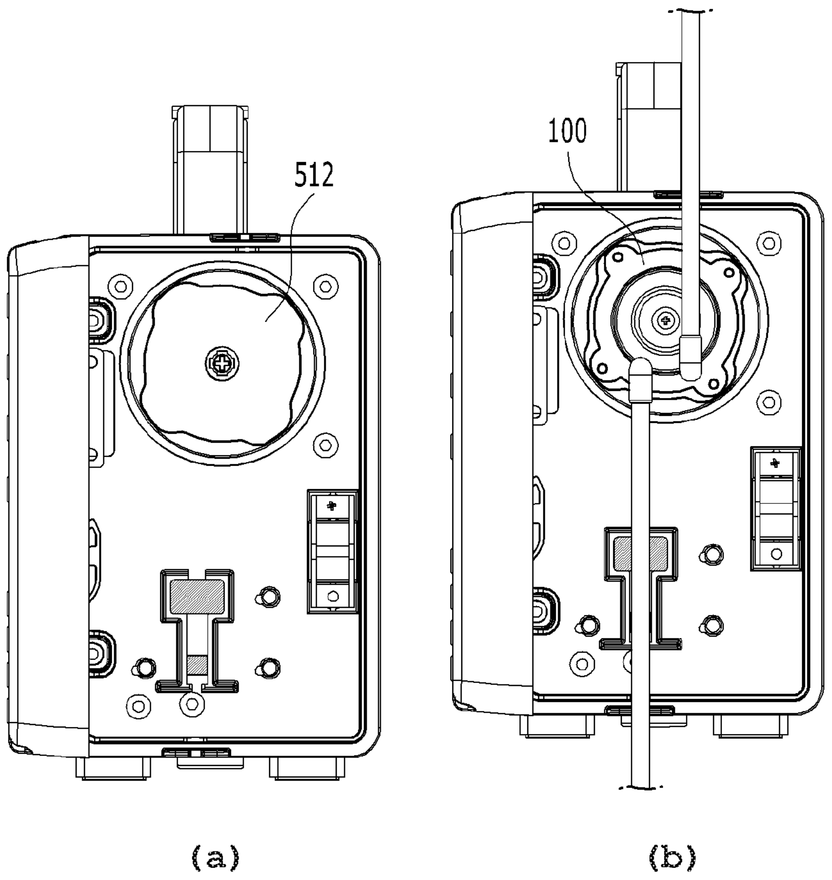
FIG. 3 is front views showing a state where the cylinder cartridge is mounted onto the cylinder pump of FIG. 1.
Figure 4:
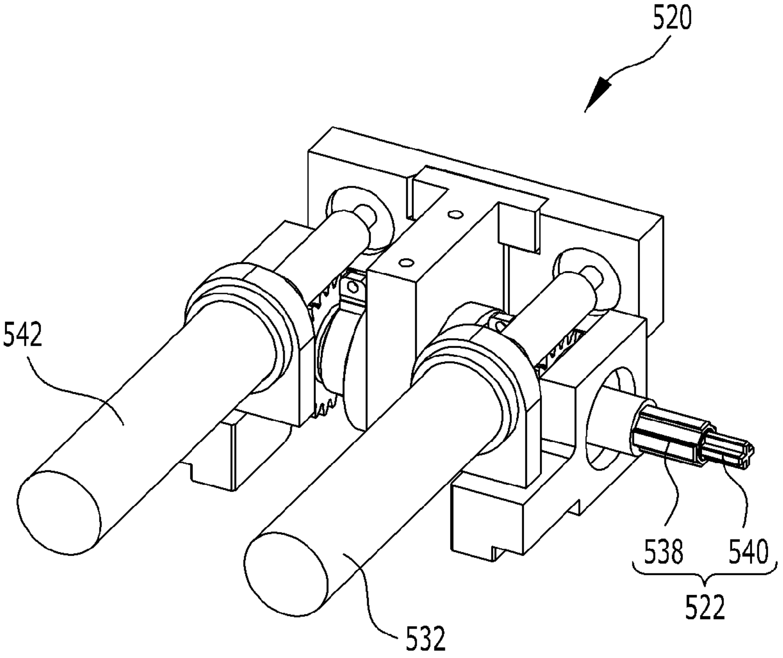
FIG. 4 is a perspective view showing a cylinder driving part of the cylinder pump of FIG. 1.
Figure 5:
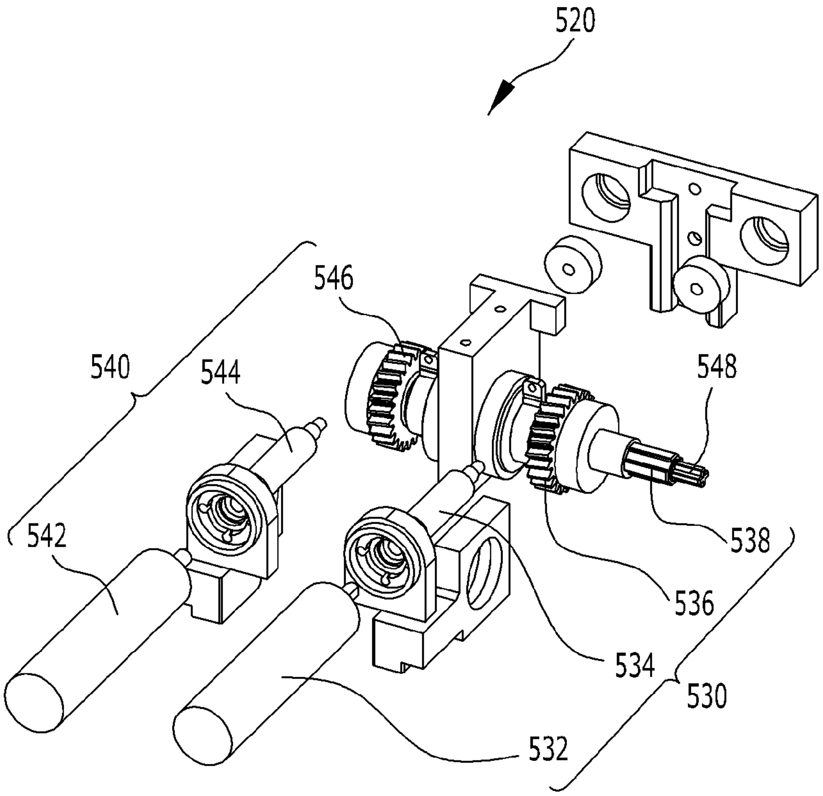
FIG. 5 is an exploded perspective view showing the cylinder driving part of FIG. 4.

Referring to FIG. 3(*a*), the driving shaft 522 appears at the center of a cartridge mounting groove 512, and the cylinder driving part 520, which is disposed inside a body of the cylinder pump 500, is shown in FIGS. 4 and 5. The cylinder driving part 520 has two driving motors adapted to operate a first driving shaft 538 and a second driving shaft 548 independently of each other, and the first driving shaft 538 and the second driving shaft 548 are configured to have a structure of a double shaft in which the second driving shaft 548 is inserted into the first driving shaft 538, while having a rotating axis corresponding to the rotating axis of the first driving shaft 538, and accordingly, they look like one driving shaft 522 on the outer appearance thereof.

FIG. 5 is an exploded perspective view showing the cylinder driving part 520. The cylinder driving part 520 includes a first driving part 530 and a second driving part 540 having worm gear structures. In specific, the first driving part 530 includes a first driving motor 532, a first worm 534 coupled to a shaft of the first driving motor 532, a first worm gear 536 engaging with the first worm 534, and the first driving shaft 538 extending vertically from the teeth of the first worm gear 536. The second driving part 540 includes a second driving motor 542, a second worm 544, a second worm gear 546, and the second driving shaft 548 in the same structure as the first driving part 530.

In specific, the cylinder driving part 520 as shown in FIG. 5 has the structure of the double shaft in which the second driving shaft 548 is inserted into the first driving shaft 538. That is, the first driving shaft 538 is hollow, and the second driving shaft 548 enters the hollow first driving shaft 538 and protrudes outward from the first driving shaft 538. Even though the cylinder driving part 520 has the structure of the double shaft, the first driving part 530 and the second driving part 540 have the worm gear structures, and accordingly, even if any one of the first driving shaft 538 and the second driving shaft 548 rotates, the other driving shaft does not rotate. Therefore, the first driving shaft 538 and the second driving shaft 548 operate independently of each other.

Referring to FIGS. 2, 4 and 5, further, the outer peripheral surface of the first driving shaft 538 corresponds to the shape of the first driving shaft fastening hole 116 formed on the upper rotation member 114 of the cylinder cartridge 100, and the end of the second driving shaft 548 corresponds to the shape of the second driving shaft fastening hole 124 formed on the lower rotation member 122. In this case, the first driving shaft fastening hole 116 is larger than the second driving shaft fastening hole 124, and the second driving shaft 548 protrudes outward from the first driving shaft 538. If the cylinder cartridge 100 is mounted on the cartridge mounting groove 512, accordingly, the second driving shaft 548 passes through the first driving shaft fastening hole 116 via the driving shaft insertion hole 112 of the cylinder cartridge 100 and is then fastened to the second driving shaft fastening hole 124 of the lower rotation member 122 located at the inner side with respect to the first driving shaft fastening hole 116, and the first driving shaft 538 is fastened to the first driving shaft fastening hole 116. As the first driving shaft 538 and the second driving shaft 548 operate independently of each other, the first piston 140 coupled to the upper rotation member 114 rotates independently of the second piston 150 by means of the first driving part 530, and the second piston 142 coupled to the lower rotation member 122 rotates independently of the first piston 140 by means of the second driving part 540.

The operating principle of the cylinder pump 500 as shown in FIGS. 1 to 5 under the above-mentioned configuration is suggested in FIGS. 6*a* to 6*h*.

The cylinder pump 500 as the prior art patent is configured to allow the rotating operations of the first piston 140 and the second piston 142 of the cylinder cartridge 100 to be controlled by means of the operation of the cylinder driving part 520, so that an intravenous drug (blood, a medical liquid, or the like) passes through the cylinder cartridge 100 and is then discharged to the outside, that is, infused into a patient. The suction and discharge of the intravenous drug are performed with an infusion cycle and an alternation cycle.

Figure 6:
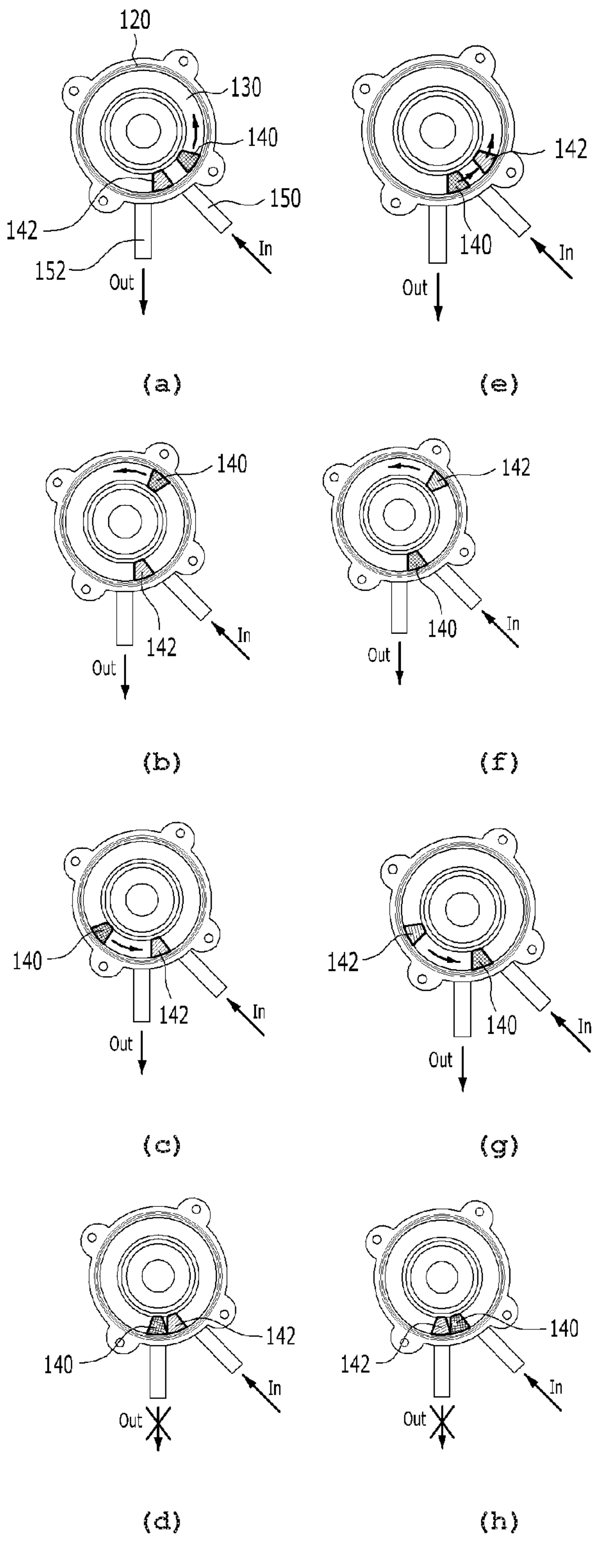
FIG. 6 is bottom views showing introducing and discharging processes performed in the cylinder cartridge.

For example, when the cylinder pump 500 initially operates, as shown in FIG. 6(*a*), so as to perform the infusion cycle, a controller of the cylinder pump 500 fixes the second piston 142 to a position between the inlet tube 150 and the outlet tube 152 and rotates the first piston 140 located close to the inlet tube 150 in a counterclockwise direction, so that a negative pressure is formed in the cylinder space 130 between the first piston 140 and the second piston 142. By the formation of the negative pressure, the intravenous drug is introduced into the cylinder cartridge 100 through the inlet tube 150.

Further, as shown in (b) and (c) of FIG. 6, as the first piston 140 is kept rotating in the counterclockwise direction, the intravenous drug is introduced into the cylinder cartridge 100 through the inlet tube 150, and the intravenous drug in the cylinder cartridge 100 is discharged to the outside through the outlet tube 152, so that the intravenous drug is kept moving (that is, introduced and discharged).

After that, as shown in FIG. 6(*d*), if the first piston 140 rotates and is thus located on the outlet tube 152, the intravenous drug in the cylinder cartridge 100 is not discharged to the outside. In this case, the controller operates the first piston 140 and the second piston 142 simultaneously, and as shown in FIG. 6(*e*), the first piston 140 is located between the inlet tube 150 and the outlet tube 152, at which the second piston 142 has been located before, and the second piston 142 rotates in the counterclockwise direction. As a result, the alternation cycle is performed to change the operations (fixing and rotating) of the first piston 140 and the second piston 142 to each other.

After the alternation cycle has been performed, as shown in (f) and (g) of FIG. 6, the controller performs the injection cycle through which the second piston 142 rotates in the counterclockwise direction in a state where the first piston 140 is fixed, and of course, as shown in FIG. 6(*h*), if the second piston 142 rotates and reaches the outlet tube 152, the controller performs the alternation cycle again to allow the operations of the first piston 140 and the second piston 142 to be alternately performed.

The introduction and discharge of the intravenous drug through the infusion cycle performed by the first piston 140 and the second piston 142 correspond to the volume of the cylinder cartridge 100 corresponding to the rotation angles of the pistons. Accordingly, the rotating speeds and angles of the first piston 140 and the second piston 142 are controlled to accurately maintain the infusion speed and amount of the intravenous drug discharged by the cylinder pump 500 (for example, encoder motors are used as the first piston 140 and the second piston 142). That is, the cylinder pump 500 accurately controls the flow rate of the intravenous drug passing through the cylinder cartridge 100, as a set value, and it means that the cylinder pump 500 as the prior art patent has a bolus function of accurately infusing the intravenous drug into the patient at the set infusion speed and amount.

The cylinder pump 500 has some advantages as well as the bolus function. One of the advantages is that the cylinder cartridge 100 has a closed system independently of the cylinder pump 500. That is, if an infusion tube and an intravenous drug pack are connected to the inlet tube 150 and the outlet tube 152 of the cylinder cartridge 100, the cylinder cartridge 100 can be mounted on the cylinder pump 500. If the cylinder cartridge 100, the infusion set, and all kinds of medicines such as an anticancer agent bind up to an intravenous drug dispensing kit in a clean environment, they can be used anytime, thereby basically preventing contamination or infection from occurring.

Another of the advantages is that the cylinder pump 500 operates through the rotating operations of the first piston 140 and the second pistons 142 of the cylinder cartridge 100. Accordingly, there is no need to exchange a syringe with new one even though the cylinder pump 500 is used for one patient for a few days, unlike a syringe pump, and further, there is no need to adjust a position where the infusion tube is pressurized periodically so as to avoid the infusion amount of the intravenous drug from being changed owing to the deformation of the infusion tube, unlike the infusion pump, so that the cylinder pump 500 can be continuously used for long hours, without any stop.

Figure 7:
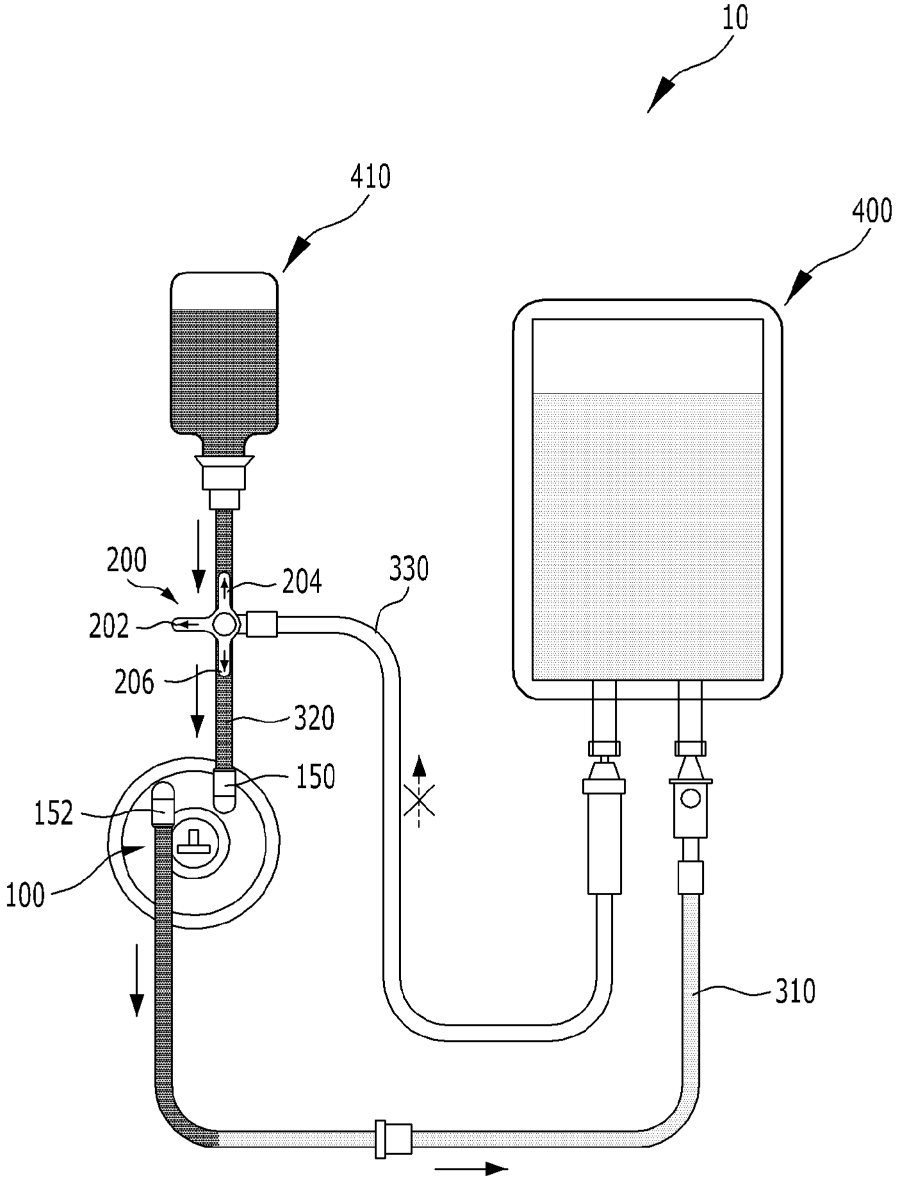
FIG. 7 is a schematic view showing an intravenous drug dispensing kit according to a first embodiment of the present invention.

The intravenous drug dispensing kit 10 and the intravenous drug dispensing system 1000 having the same according to the present invention are derived from the specific configuration in which the cylinder pump 500 invented by the same applicant as the invention performs accurate bolus control through active suction and discharge of the intravenous drug and the cylinder cartridge 100 has the closed system independently of the cylinder pump 500. FIG. 7 shows an intravenous drug dispensing kit according to a first embodiment of the present invention.

Referring to FIG. 7, the intravenous drug dispensing kit 10 according to the first embodiment of the present invention is configured to have a cylinder cartridge 100, first to fourth tubes and a three-way valve 200 connected to the cylinder cartridge 100, and an infusion pack 400 and a medical liquid container 410 with a medical liquid mixed with a fluid in the infusion pack 400, which are coupled to the first to fourth tubes and the three-way valve 200. Using the intravenous drug dispensing kit 10, a prescribed amount of the medical liquid is accurately mixed with the fluid in the infusion pack 400 (or a nutrient pack, which is representatively called the infusion pack), thereby dispensing the intravenous drug. Further, the first to fourth tubes of the intravenous drug dispensing kit 10 are transparent tubes, that is, infusion tubes generally used, to check the flows of the fluid and the medical liquid.

The intravenous drug dispensing kit 10 includes the cylinder cartridge 100 that introduces and discharges external fluids through changes in the volume of a cylinder occurring when a pair of first and second pistons 140 and 142 disposed therein is fixed and rotates relatively to each other. A configuration of the cylinder cartridge 100 is the same as mentioned above.

Further, the first tube 310 is connected to the outlet tube 152 of the cylinder cartridge 100, and a discharge flow path 206 of the three-way valve 200 is connected to the inlet tube 150 of the cylinder cartridge 100 via the second tube 320. Any one of two introducing flow paths of the three-way valve 200 is connected to the discharge flow path 206, so that the flows along the two flow paths can be selectively open or stopped. The third tube 330 is connected to the first introducing flow path 202, and the fourth tube 340 is connected to the second introducing flow path 204.

Under the configuration of the intravenous drug dispensing kit 10, one flow in one direction toward the outlet tube 152 of the cylinder cartridge 100 is formed through the first tube 310, but the flow along any one of the third tube 330 and the fourth tube 340 is introduced through the operation of the three-way valve 200 into the inlet tube 150 of the cylinder cartridge 100. That is, any one of the two types of liquids is selected and flows to the inlet tube 150 of the cylinder cartridge 100, and the selected liquid is discharged through the outlet tube 152.

To allow a prescribed amount of the medical liquid such as an anticancer agent to be accurately mixed with the fluid in the infusion pack 400 to thus dispense the intravenous drug, the intravenous drug dispensing kit 10 according to the first embodiment of the present invention is configured to connect the infusion pack 400 to the first tube 310 and the second tube 330 and connect the medical liquid container 410 to the fourth tube 340. Accordingly, the fluid in the infusion pack 400 or the medical liquid in the medical liquid container 410 selectively flows to the inlet tube 150 of the cylinder cartridge 100. Further, the fluid is discharged and introduced from and into the infusion pack 400 at the same time, but the medical liquid is just discharged from the medical liquid container 410, which will be discussed later. So as to allow the medical liquid to be gently discharged from the medical liquid container 410, accordingly, a negative pressure inside the medical liquid container 410 has to be removed. To do this, the fourth tube 340 and the medical liquid container 410 are desirably connected to each other by means of an adapter 300 having an air introducing function. Further, the adapter 300 serves as a holder for the medical liquid container 410 to basically prevent the medical liquid container 410 from being unexpectedly separated from the fourth tube 340.

Figure 9:
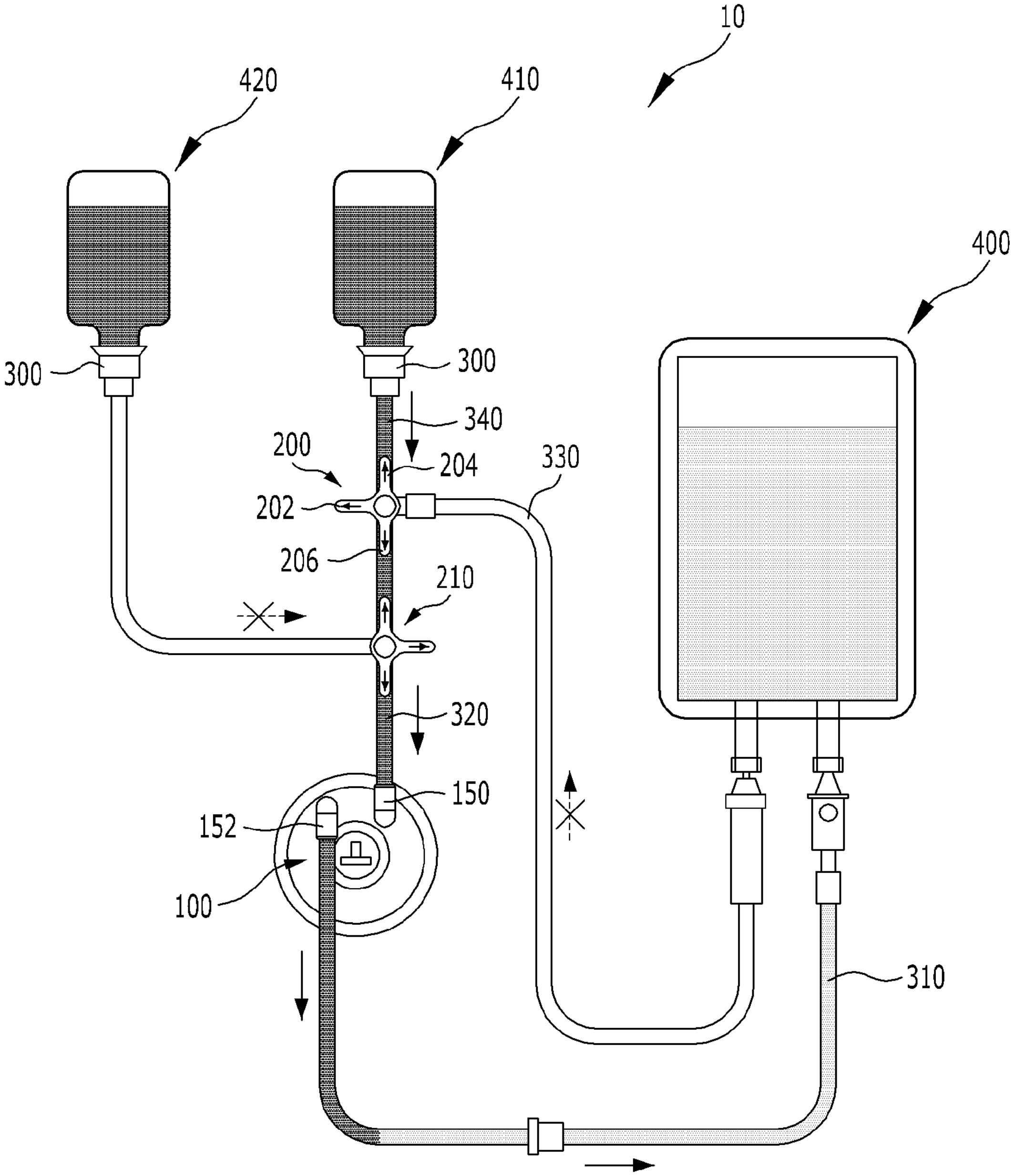
FIG. 9 is a schematic view showing an intravenous drug dispensing kit according to a second embodiment of the present invention.

Moreover, as shown in FIG. 9, an additional flow path for mixing two or more medical liquids sequentially is provided. The additional flow path includes an additional three-way valve 210, and it is possible that the additional flow path may extend to correspond to the number of additional medical liquid containers 420. A first introducing flow path and a discharge flow path of the additional three-way valve 210 are connected to any one of the second to fourth tubes 320, 330, and 340, and the additional medical liquid container 420 is connected to a second introducing flow path of the additional three-way valve 210. The respective medical liquid containers 410 and 420 are disposed in parallel with each other with respect to the inlet tube 150 of the cylinder cartridge 100.

Figure 10:
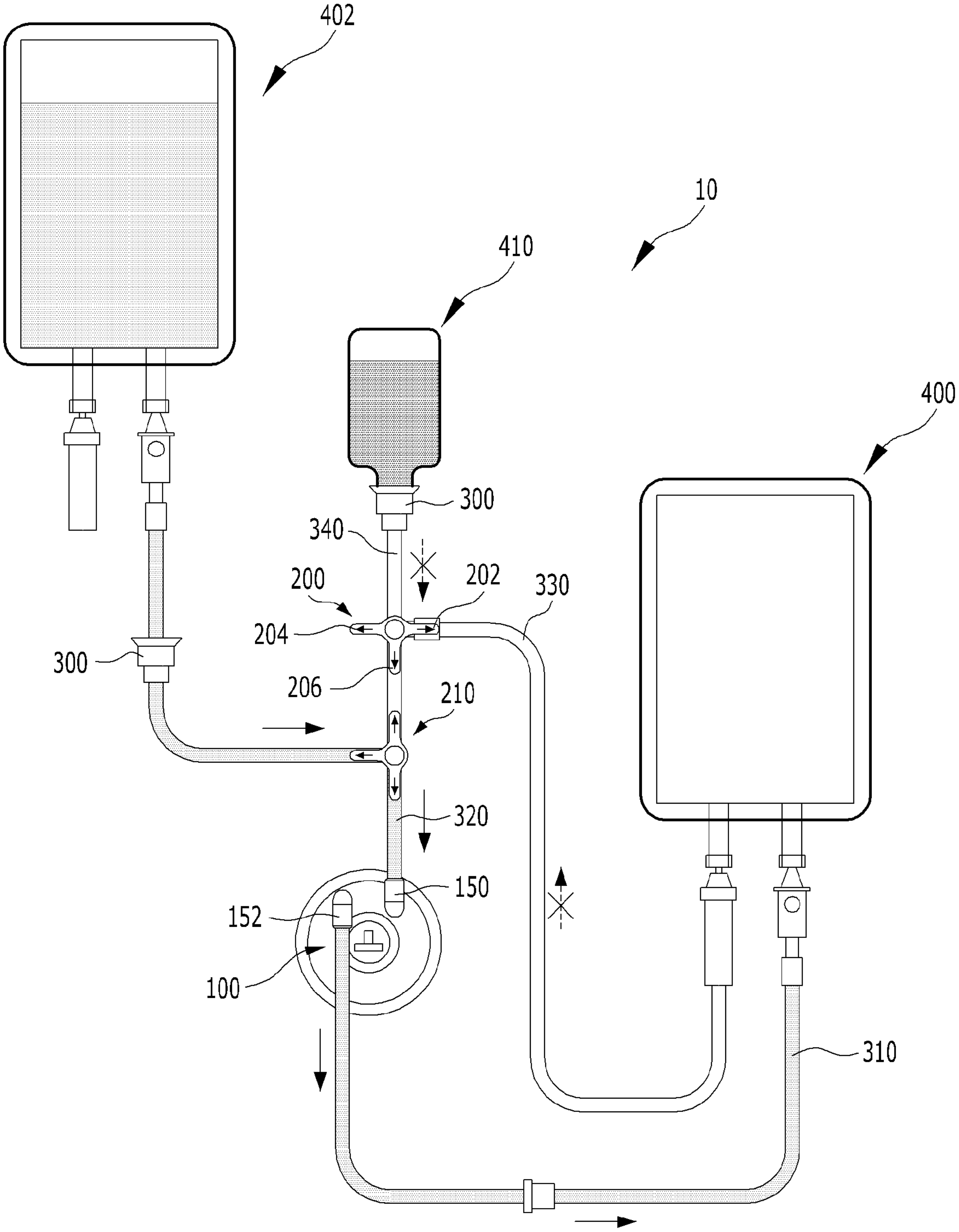
FIG. 10 is a schematic view showing an intravenous drug dispensing kit according to a third embodiment of the present invention.

Further, an intravenous drug dispensing kit 10 as shown in FIG. 10 is configured in another embodiment of the present invention, while having the same basic structure as in FIG. 9. According to another embodiment of the present invention, as shown in FIG. 10, an empty infusion pack 402 is prepared, and a fluid and a medical liquid such as an anticancer agent are introduced sequentially into the empty infusion pack 402, thereby dispensing an intravenous drug. That is, a fixed amount of medical liquid is introduced and mixed with the fluid in the infusion pack 400 in the above-mentioned embodiments of the present invention, but in the embodiment of the present invention as shown in FIG. 10, the fluid as well as the medical liquid are discharged with fixed amounts through the cylinder pump 500 to thus dispense the intravenous drug.

In specific, an infusion pack 400 is connected to a second introducing flow path of an additional three-way valve 210, and the empty infusion pack 402 to a first tube 310 and a third tube 330, and a medical liquid container 410 to a fourth tube 340. When the intravenous drug is dispensed, a discharge flow path of the additional three-way valve 210 is open to introduce the fluid of the infusion pack 400 with the fixed amount in prescription into the empty infusion pack 402, and after that, the medical liquid in the medical liquid container 410 connected to the three-way valve 200 is introduced with the fixed amount in prescription into the empty infusion pack 402 (even though the fixed amount of fluid has been introduced into the empty infusion pack 402, but the term, the empty infusion pack 402 is still used so as to be distinguished from the infusion pack 400), thereby completing intravenous drug dispensing.

In the embodiment of the present invention as shown in FIG. 10, when the intravenous drug is dispensed, advantageously, it can be dispensed as needed in the prescription, without allowing an excessive amount of fluid to be in advance discharged from the infusion pack 400 and thrown away (it is possible that an accurate amount of fluid is discharged by the cylinder pump). In the embodiment of the present invention as shown in FIG. 10, further, the additional three-way valve 210 and the additional medical liquid container 420 may be included so that a plurality of medical liquids may be mixed with the fluid, as shown in FIG. 9.

Figure 11:
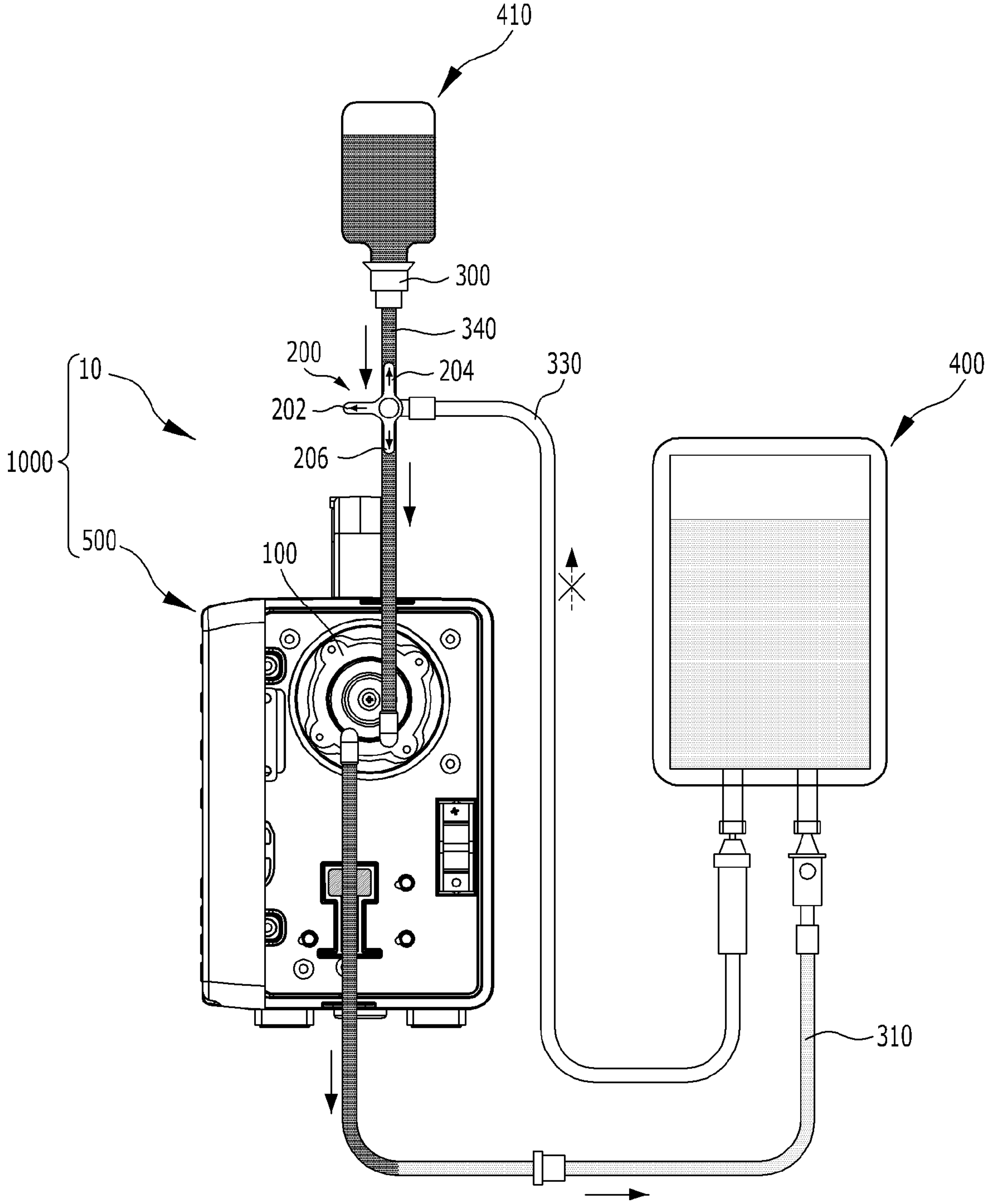
FIG. 11 is a schematic view showing an intravenous drug dispensing system in which the intravenous drug dispensing kit of FIG. 7 is coupled to the cylinder pump.

FIG. 11 shows an intravenous drug dispensing system 1000 in which the intravenous drug dispensing kit 10 is mounted on the cylinder pump 500. The intravenous drug dispensing kit 10 is one kit having a closed system in which the infusion pack 400 and the medical liquid container 410 are connected to the cylinder cartridge 100, and the intravenous drug dispensing system 1000 is a system that utilizes the bolus function of the cylinder pump 500 to accurately dispense the intravenous drug as prescribed.

The intravenous drug dispensing kit 10 itself is provided as one kit, and if the cylinder cartridge 100 of the intravenous drug dispensing kit 10 is mounted onto the cartridge mounting groove 512 of the cylinder pump 500, the preparation for the intravenous drug dispensing is completed. The configuration wherein the cylinder driving part 520 of the cylinder pump 500 operates the cylinder cartridge 100 is the same as in the above.

The cylinder pump 500 has a controller for controlling the cylinder driving part 520, and the controller accurately controls the amounts and flow rates of liquids introduced and discharged through the cylinder cartridge 100, with preset values. A process of mixing one medical liquid with the fluid in the infusion pack 400, without having any additional medical liquid container 420, is simplest and basic, and such mixing process is repeatedly carried out if there is an additional medical liquid.

Referring to FIG. 7, in the case of the three-way valve 200, the second introducing flow path 204 connected to the fourth tube 340 and the discharge flow path 206 connected to the second tube 320 are open. Accordingly, the medical liquid of the medical liquid container 410 flows to the inlet tube 150 of the cylinder cartridge 100, and the flow of the fluid through the third tube 330 is blocked. In this state, the controller of the cylinder pump 500 controls the cylinder driving part 520 to allow the medical liquid of the medical liquid container 410 connected to the fourth tube 340 to be introduced by the set amount and then discharged to the infusion pack 400 connected to the first tube 310.

So as to dispense the intravenous drug, in the conventional practices, the medical liquid in the medical liquid container (ampoule, and the like) is extracted with a syringe and injected into the infusion pack 400 by a pharmacy specialist, but according to the present invention, the cylinder pump 500 performs suction and discharge together so that the conventional work with the syringe is automatically achieved to reduce the labors needed, thereby greatly suppressing risk occurring when toxic medical liquids are treated, automatically performing accurate metering for the prescription and dispensing of the medical liquid such as an anticancer agent, and removing worrying about errors upon the dispensing.

According to the present invention, further, all of dispensing processes are performed while the intravenous drug dispensing kit 10 is kept to the closed system, and accordingly, conventional processes of inserting and drawing a needle are not needed, thereby advantageously removing risk of contamination of the infusion pack 400. So as to ensure the closed state of the intravenous drug dispensing kit 10, in this case, needless valves are desirably mounted on connection portions with all of the tubes and automatically converted into locked states when separated from the connection portions.

Now, an explanation of a method for dispensing an intravenous drug as prescribed by using the intravenous drug dispensing kit 10, the cylinder pump 500, and the adapter 300 having an air introducing function will be given. In this case, the cylinder pump 500 is not suggested in the drawings for explaining the intravenous drug dispensing method, which is just for the convenience of the description, and therefore, it should be understood that the cylinder pump 500 is absolutely used to operate the cylinder cartridge 100. Further, the intravenous drug dispensing method is performed in an aseptic facility.

After the intravenous drug dispensing kit 10 as shown in FIG. 7 is first prepared, the infusion pack 400 is connected to the first tube 310 and the third tube 330, and the medical liquid container 410 is connected to the fourth tube 340. Of course, the fluid and the medical liquid as prescribed by a doctor are used. Next, the cylinder cartridge 100 of the intravenous drug dispensing kit 10 sterilized and packed is coupled to the cartridge mounting groove 512 of the cylinder pump 500. Accordingly, the first and second pistons 140 and 142 disposed inside the cylinder cartridge 100 operate independently of each other by means of the cylinder driving part 520 of the cylinder pump 500.

If the intravenous drug dispensing kit 10 is mounted onto the cylinder pump 500, an amount of the medical liquid to be dispensed as prescribed is checked by a producer (a pharmacy specialist), and next, the amount of the medical liquid to be introduced into the infusion pack 400 is inputted to the controller of the cylinder pump 500. In this case, the three-way valve 200 operates to open the second introducing flow path 204 connected to the fourth tube 340 and the discharge flow path 206 connected to the second tube 320.

If such preparation is done, the cylinder pump 500 operates to introduce the medical liquid in the medical liquid container 410 into the infusion pack 400 by the set amount, and if the medical liquid flows to the infusion pack 400 by the set amount, the cylinder pump 500 stops.

The above processes are basic processes of dispensing the intravenous drug. Additionally, the set amount of medical liquid may remain inside the first tube 310 and the second tube 320, without being all introduced into the infusion pack 400. To introduce the remaining medical liquid into the infusion pack 400, a process of circulating the fluid in the infusion pack 400 is needed. To form a circulation flow path of the fluid by the operation of the three-way valve 200, that is, the first introducing flow path connected to the third tube 330 and the discharge flow path 206 connected to the second tube 320 are open, and next, the cylinder pump 500 operates to circulate the fluid in the infusion pack 400 through the cylinder cartridge 100, so that the medical liquid remaining in the tubes is completely introduced into the infusion pack 400.

Figure 8:
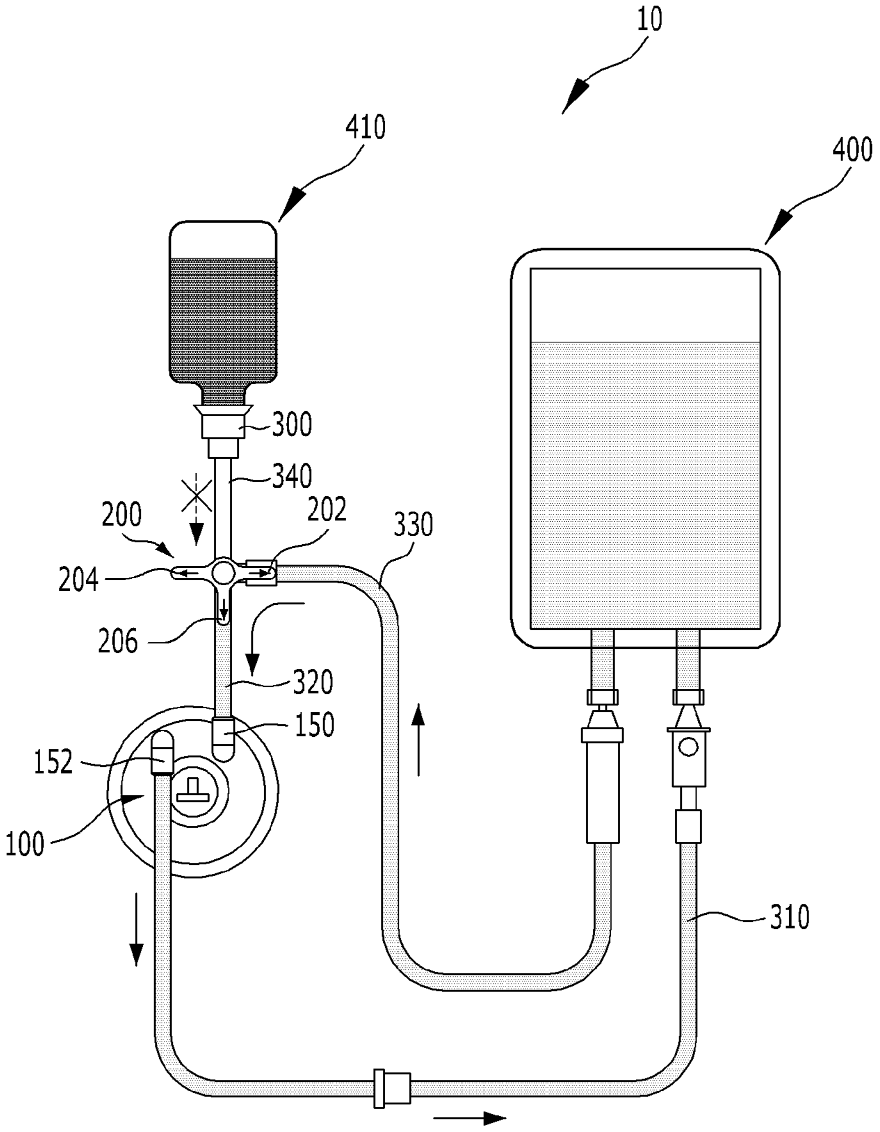
FIG. 8 is a schematic view showing a state where a three-way valve is changed in flow path in the intravenous drug dispensing kit of FIG. 7.

The medical liquid of the medical liquid container 410 is first sucked and discharged in the above-mentioned description, and before the process, in this case, a priming process of removing air from the first to third tubes 310, 320 and 330 is carried out. The priming process is similar to the above-mentioned process of circulating the fluid in the infusion pack 400, which is shown in FIG. 8. The three-way valve 200 operates to open the first introducing flow path connected to the third tube 330 and the discharge flow path 206 connected to the second tube 320, and accordingly, the fluid in the infusion pack 400 is circulated through the cylinder cartridge 100, so that the air inside the first to third tubes 310, 320 and 330 is removed.

Further, the process of mixing one medical liquid with the fluid has been basically performed in the above-mentioned description, but of course, it is possible that two or more medical liquids may be mixed with the fluid in the infusion pack 400.

For example, the medical liquid container 410 from which the medical liquid is extracted is replaced with another additional medical liquid container 420, and next, an amount of a medical liquid of the medical liquid container 420 as prescribed is inputted to introduce the medical liquid in the medical liquid container 420 into the infusion pack 400 by the set amount. Such processes are repeatedly carried out by the types of medical liquids as prescribed.

However, it is not desirable that the plurality of medical liquid containers are repeatedly coupled to and separated from one ampoule adapter 300 because of the contamination of the adapter 300. Accordingly, the intravenous drug dispensing kit 10 of the present invention is configured as shown in FIG. 9 so that extraction processes are performed sequentially, without replacing one medical liquid container 410 with another medical liquid container 420.

That is, the first introducing flow path and the discharge flow path of at least one additional three-way valve 210 is connected to any one (the second tube in FIG. 9) of the second to fourth tubes 320, 330, and 340, and the additional medical liquid container 420 is connected to the second introducing flow path of the additional three-way valve 210, thereby preparing one intravenous drug dispensing kit 10. After that, if the extraction process from the medical liquid container 410 is completed, the discharge flow path 206 of the medical liquid container 410 is closed, and the discharge flow path of the additional medical liquid container 420 is open. Next, the cylinder pump 500 operates to introduce the medical liquid in the additional medical liquid container 420 by the set amount into the infusion pack 400, thereby completing a series of intravenous drug dispensing processes.

Further, as described in the embodiment of the present invention as shown in FIG. 10, the intravenous drug may be dispensed using the empty infusion pack 402. That is, the intravenous drug dispensing kit 10 is configured so that the empty infusion pack 402 is connected to the first tube 310 and the third tube 330, the first introducing flow path and the discharge flow path of at least one additional three-way valve 210 is connected to any one of the second to fourth tubes 320, 330, and 340, and the infusion pack 400 is connected to the second introducing flow path of the additional three-way valve 210. The medical liquid container 410 is connected to the second introducing flow path 204 of the three-way valve 200 through the fourth tube 340. In this case, the plurality of additional three-way valves 210 may be provided because the additional medical liquid containers 420 are provided.

In the prepared intravenous drug dispensing kit 10, the fluid in the infusion pack 400 connected to the second introducing flow path of the additional three-way valve 210 is introduced into the empty infusion pack 402 by the set amount, and while the discharge flow path of the infusion pack 400 is being closed, the discharge flow path 206 of the three-way valve 200 to the medical liquid container 410 is open to introduce the medical liquid in the medical liquid container 410 into the empty infusion pack 402 by the set amount, thereby completing the intravenous drug dispensing.

Figure 12:
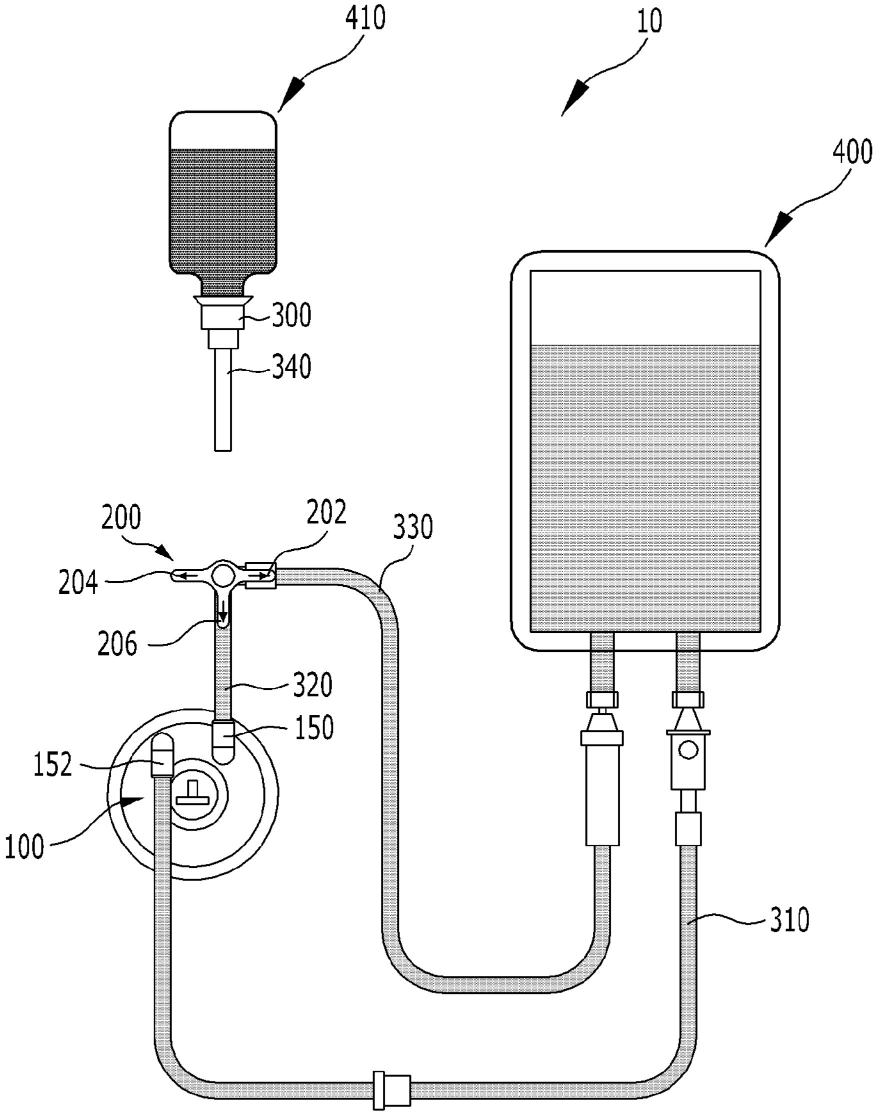
FIG. 12 is a schematic view showing one state where a finishing step for an infusion pack is carried out after intravenous drug dispensing is completed.
Figure 13:
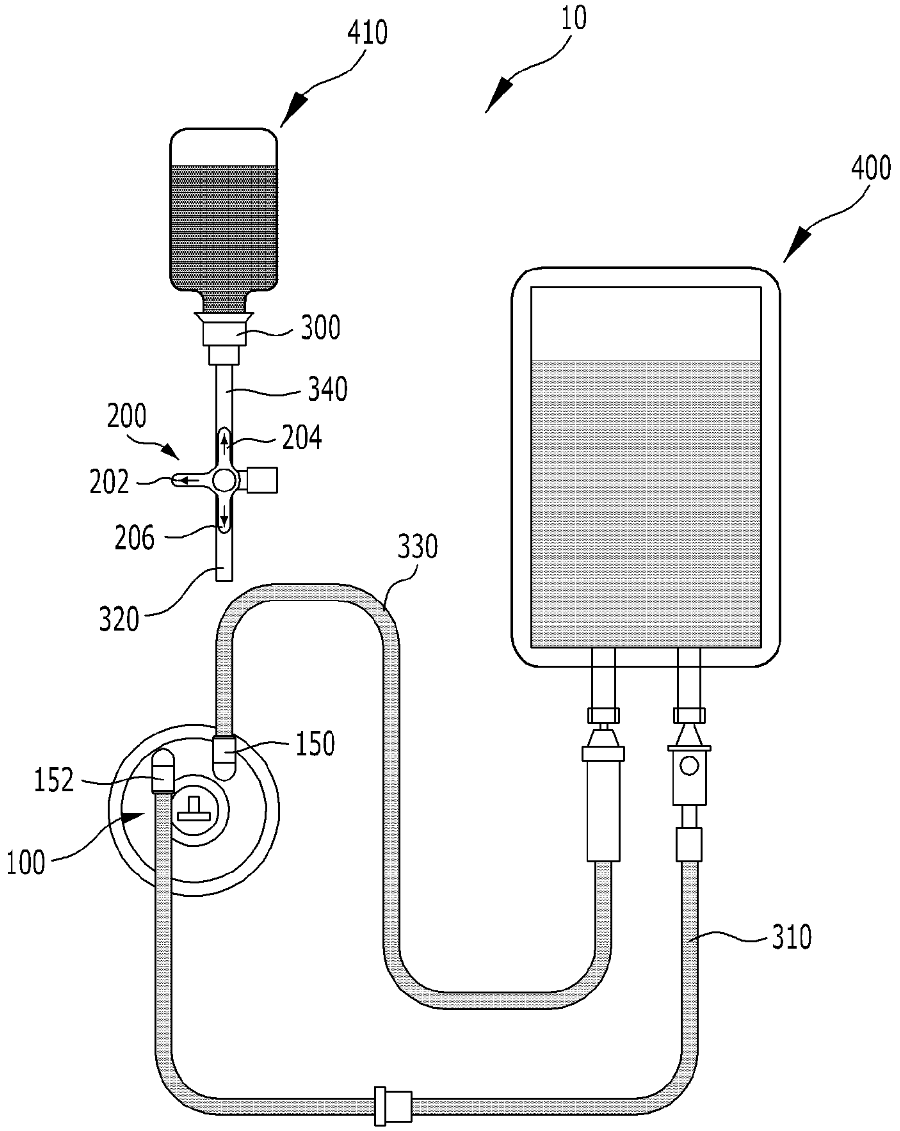
FIG. 13 is a schematic view showing another state where a finishing step for an infusion pack is carried out after intravenous drug dispensing is completed.

If the intravenous drug dispensing using the cylinder pump 500 is completed, finishing steps as shown in FIGS. 12 and 13 are performed. FIG. 12 shows one finishing step wherein the medical liquid container 410 and the fourth tube 340 are removed from the cylinder cartridge 100 and the second introducing flow path 204 of the three-way valve 200 connected to the fourth tube 340 is closed. Otherwise, FIG. 13 shows another finishing step wherein the medical liquid container 410, the fourth tube 340, and the second tube 320 are removed from the cylinder cartridge 100 and the third tube 330 is connected to the inlet tube 150.

To prevent the infusion pack 400 from being contaminated before used for the patient, the ends of all of the tubes have to be sterilized and sealed. Accordingly, the infusion pack 400 dispensed in an aseptic environment is subjected to the finishing step, and accordingly, the intravenous drug dispensing kit 10 is kept to the closed state around the cylinder cartridge 100, thereby solving problems of contamination and infection. Just before the prepared infusion pack 400 is infused into the patient, the tube connected to the outlet tube 152 when the cylinder cartridge 100 is mounted onto the cylinder pump 500 is connected to the patient's catheter, and after an amount of intravenous drug as prescribed is inputted to the controller of the cylinder pump 500, the cylinder pump 500 operates to start the infusion.

Figure 14:
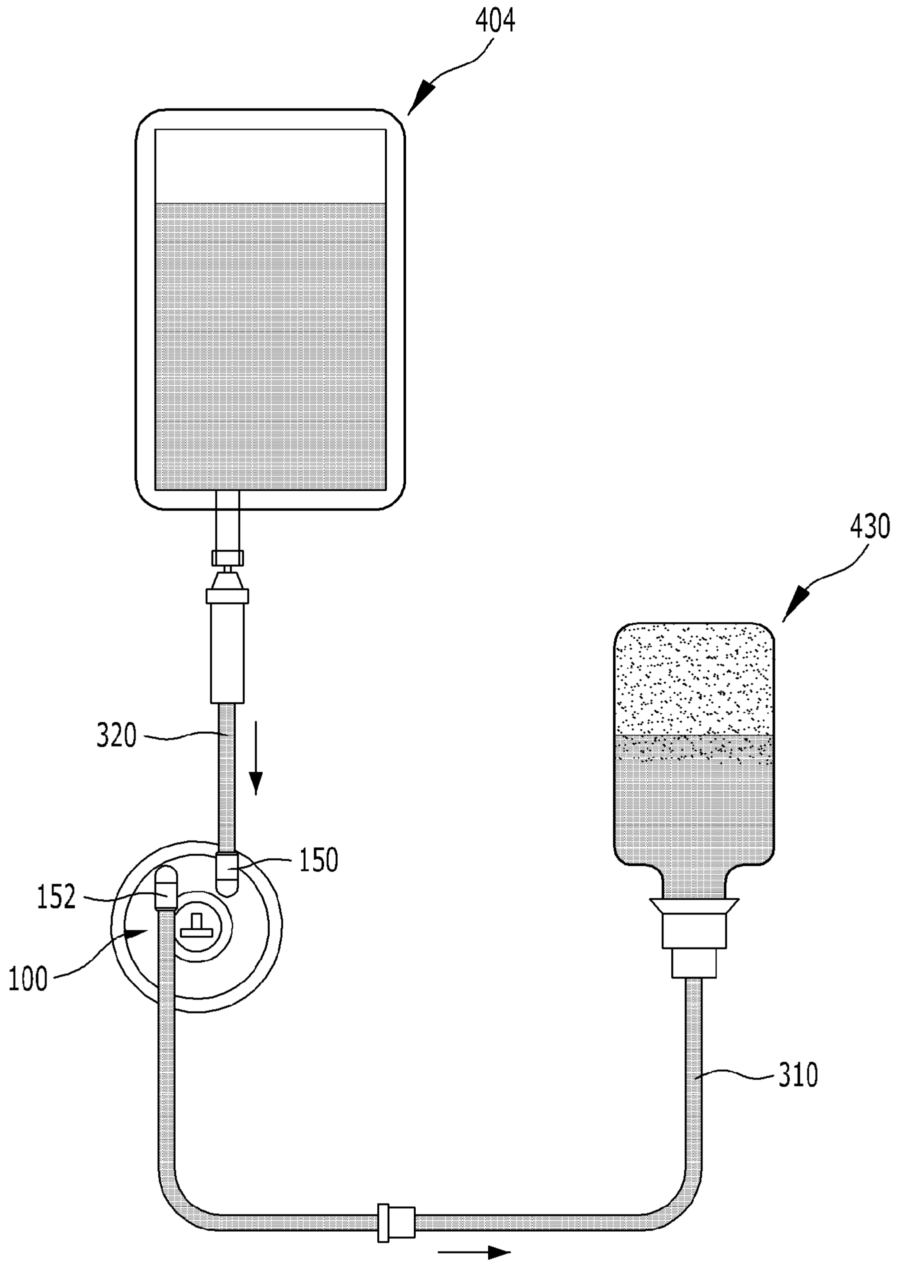
FIG. 14 is a schematic view showing a modification of the intravenous drug dispensing kit according to the present invention.

Further, FIG. 14 shows a modification of the intravenous drug dispensing kit 10 according to the present invention. In the embodiment of the present invention, as shown in FIG. 14, the medical liquid such as an anticancer agent is provided in powder form. The powdered medicine has to be melt and diluted by a fluid so as to perform intravenous injection, and a dilution rate of the powdered medicine is written in the prescription. Even in this case, the present invention can mix an accurate amount of a diluent with the fluid through the cylinder pump 500, and to do this, the intravenous drug dispensing kit 10 is shown in FIG. 14.

The cylinder pump 500 is used for the liquid (medical liquid), and accordingly, it does not suck and discharge the powdered medicine. The intravenous drug dispensing kit 10 applicable to the powdered medicine is configured to mount a powdered medicine container 430 onto the first tube 310 connected to the outlet tube 152 of the cylinder cartridge 100 and to connect a diluent pack 404 to the second tube 320 connected to the inlet tube 150 of the cylinder cartridge 100. In the intravenous drug dispensing kit 10 applicable to the powdered medicine, the cylinder pump 500 operates to suck the diluent inside the diluent pack 404 by a set amount and to then introduce the sucked diluent into the powdered medicine container 430. The powdered medicine container 430 into which the diluent is introduced swings appropriately so that the powdered medicine is dissolved sufficiently.

In this case, the diluent pack 404 is a container in which the diluent is stored. Of course, the fluid in the infusion pack 400 may be used as the diluent, but since the diluent may be differently used according to the properties of the powdered medicine, the term, the diluents pack 404 is used.

Further, the dissolved powdered medicine can be treated in the same manner as the general medical liquid as mentioned above, and accordingly, the powdered medicine container 430 after the dissolution process is used in the same manner as the medical liquid container 410 or the additional medical liquid container 420 as mentioned in FIGS. 7 to 13, so that the dissolved powdered medicine is mixed with the fluid in the infusion pack 400 or introduced into the empty infusion pack 402 to dispense the intravenous drug.

While the foregoing examples are illustrative of the principles according to the present invention in one or more particular applications, it will be apparent to those of ordinary skill in the art that numerous modifications in form, usage and details of implementation can be made without the exercise of inventive faculty, and without departing from the principles and concepts of the invention. It is therefore intended that the scope of the invention be limited not by this detailed description, but rather by the claims appended hereto.

EXPLANATIONS OF REFERENCE NUMERALS IN THE DRAWINGS

10: Intravenous drug dispensing kit 100: Cylinder cartridge
110: Upper housing 112: Driving shaft insertion hole
114: Upper rotation member 116: First driving shaft fastening hole
118: Upper fastening member 120: Lower housing
122: Lower rotation member 124: Second driving shaft fastening hole
126: Lower fastening member 130: Cylinder space
140: First piston 142: Second piston
150: Inlet tube 152: Outlet tube
200: Three-way valve 202: First introducing flow path
204: Second introducing flow path 206: Discharge flow path
210: Additional three-way valve 300: Medical liquid container adapter
310: First tube 320: Second tube
330: Third tube 340: Fourth tube
400: Infusion pack 402: Empty infusion pack
404: Diluent pack 410: Medical liquid container
420: Additional medical liquid container 430: Powdered medicine container
500: Cylinder pump 510: Cover
512: Cartridge mounting groove 520: Cylinder driving part
522: Driving shaft 530: First driving part
532: First driving motor 534: First worm
536: First worm gear 538: First driving shaft
540: Second driving part 542: Second driving motor
544: Second worm 546: Second worm gear
548: Second driving shaft 1000: Intravenous drug dispensing system

The invention claimed is:

1. An intravenous drug dispensing kit comprising:

a cylinder cartridge for introducing and discharging external fluids through changes in the volume of a cylinder occurring when a pair of first and second pistons disposed therein is fixed and rotates relatively to each other;

a first tube connected to an outlet tube of the cylinder cartridge;

a three-way valve having a first introducing flow path, a second introducing flow path, and a discharge flow path connected to any one of the first introducing flow path and the second introducing flow path;

a second tube for connecting the discharge flow path of the three-way valve to an inlet tube of the cylinder cartridge;

a third tube connected to the first introducing flow path of the three-way valve; and a fourth tube connected to the second introducing flow path of the three-way valve, wherein the first tube and the third tube are connected to an infusion pack, wherein the fourth tube is connected to a medical liquid container, and wherein, in a valve-open dispensing configuration of the three-way valve in which the second introducing flow path connected to the fourth tube and the discharge flow path connected to the second tube are open, the fourth tube is fluidly connected to the second tube through the three-way valve such that a flow path extends from the medical liquid container to the infusion pack through the fourth tube, the second tube, the cylinder cartridge, and the first tube.

2. The intravenous drug dispensing kit according to claim 1, wherein the fourth tube and the medical liquid container are connected to each other by an adapter having an air introducing function.

3. The intravenous drug dispensing kit according to claim 2, wherein the adapter is configured to serve as a holder for the medical liquid container to prevent the medical liquid container from being unexpectedly separated from the fourth tube.

4. The intravenous drug dispensing kit according to claim 1, further comprising at least one or more additional three-way valve, each additional three-way valve having a first introducing flow path and a discharge flow path connected to any one of the second tube, the third tube, and the fourth tube.

5. The intravenous drug dispensing kit according to claim 4, wherein the additional three-way valve has a second introducing flow path connected to an additional medical liquid container.

6. The intravenous drug dispensing kit according to claim 4, wherein the additional three-way valve has a second introducing flow path connected to the infusion pack, the first tube and the third tube are connected to an empty infusion pack, and the fourth tube is connected to the medical liquid container.

7. The intravenous drug dispensing kit according to claim 1, wherein the cylinder cartridge comprises an upper rotation member and a lower rotation member freely rotatable relative to each other, while forming a circular cylinder space between the upper rotation member and the lower rotation member, and wherein the first piston is coupled to the upper rotation member to rotate along the cylinder space, while the second piston is coupled to the lower rotation member to rotate along the cylinder space.

8. An intravenous drug dispensing system comprising:

the intravenous drug dispensing kit as defined in claim 1; and a cylinder pump for mounting the cylinder cartridge of the intravenous drug dispensing kit thereon to drive the pair of first and second pistons disposed inside the cylinder cartridge independently of each other.

9. The intravenous drug dispensing system according to claim 8, wherein the cylinder pump comprises a cylinder driving part for driving the pair of first and second pistons disposed inside the cylinder cartridge independently of each other and a controller for controlling the cylinder driving part, and wherein the controller controls amounts and flow rates of the liquids introduced and discharged through the cylinder cartridge, with preset values.

10. The intravenous drug dispensing system according to claim 9, wherein, in the valve-open dispensing configuration of the three-way valve in which the second introducing flow path connected to the fourth tube and the discharge flow path connected to the second tube are open, the controller of the cylinder pump controls the cylinder driving part to introduce a present amount of the medical liquid in the medical liquid container through the fourth tube and the second tube into the cylinder cartridge to discharge the present amount of the medical liquid through the first tube to the infusion pack.

11. The intravenous drug dispensing system according to claim 10, wherein, while the second introducing flow path connected to the fourth tube and the discharge flow path connected to the second tube are open on the three-way valve, the discharge flow path is not connected to the first introducing flow path connected to the third tube, thereby blocking fluid flow through the third tube.

12. The intravenous drug dispensing system according to claim 9, wherein the cylinder cartridge comprises an upper rotation member and a lower rotation member, and wherein the cylinder driving part comprises a first driving part for operating the upper rotation member of the cylinder cartridge and a second driving part for operating the lower rotation member of the cylinder cartridge, the cylinder driving part having a structure of a double shaft in which a second driving shaft of the second driving part is inserted into a first driving shaft of the first driving part.

13. The intravenous drug dispensing system according to claim 12, wherein the first driving part and the second driving part have worm gear structures.

14. An intravenous drug dispensing method comprising:

a first step of preparing the intravenous drug dispensing kit as defined in claim 1, connecting the infusion pack to the first tube and the third tube, and connecting the medical liquid container to the fourth tube;

a second step of mounting the cylinder cartridge of the intravenous drug dispensing kit onto a cylinder pump for driving the pair of first and second pistons disposed inside the cylinder cartridge independently of each other;

a third step of inputting an amount of the medical liquid in the medical liquid container to be introduced into the infusion pack to the cylinder pump;

a fourth step of opening the second introducing flow path connected to the fourth tube and the discharge flow path connected to the second tube, on the three-way valve; and a fifth step of operating the cylinder pump to introduce the medical liquid in the medical liquid container into the infusion pack by a set amount.

15. The intravenous drug dispensing method according to claim 14, wherein after the fifth step, to form a circulation flow path of the fluid in the infusion pack by the operation of the three-way valve, the first introducing flow path connected to the third tube and the discharge flow path connected to the second tube are open on the three-way valve, and the cylinder pump operates to circulate the fluid in the infusion pack through the cylinder cartridge, so that the medical liquid remaining in the tubes is completely introduced into the infusion pack.

16. The intravenous drug dispensing method according to claim 14, further comprising, between the third step and the fourth step, a priming step of removing air from the first to third tubes.

17. The intravenous drug dispensing method according to claim 16, wherein the priming step is performed to open the first introducing flow path connected to the third tube and the discharge flow path connected to the second tube on the three-way valve and to circulate the fluid in the infusion pack through the cylinder cartridge, so that the air inside the first to third tubes is removed.

18. The intravenous drug dispensing method according to claim 14, further comprising, after the medical liquid container is replaced with an additional medical liquid container, a step of operating the cylinder pump to introduce the medical liquid in the additional medical liquid container into the infusion pack by a set amount.

19. The intravenous drug dispensing method according to claim 14, wherein the first step comprises a step of connecting a first introducing flow path and a discharge flow path of at least one additional three-way valve to any one of the second to fourth tubes and connecting the additional medical liquid container to a second introducing flow path of the additional three-way valve, the method further comprising, after the fifth step, a mixing step of closing the discharge flow path to the medical liquid container, opening the discharge flow path to the additional medical liquid container, and operating the cylinder pump to introduce the medical liquid in the additional medical liquid container into the infusion pack by the set amount.

20. The intravenous drug dispensing method according to claim 14, wherein the first step comprises a step of connecting an empty infusion pack to the first tube and the third tube, connecting a first introducing flow path and the discharge flow path of the at least one additional three-way valve to any one of the second to fourth tubes, and connecting the infusion pack to a second introducing flow path of any one additional three-way valve, and the third to fifth steps are carried out by introducing the fluid in the infusion pack connected to the second introducing flow path of the additional three-way valve into the empty infusion pack by the set amount, closing the discharge flow path to the infusion pack, opening the discharge flow path to the medical liquid container, and introducing the medical liquid in the medical liquid container into the empty infusion pack by the set amount.

21. The intravenous drug dispensing method according to claim 14, further comprising, after the fifth step, a finishing step of removing the medical liquid container and the fourth tube from the cylinder cartridge and closing the second introducing flow path of the three-way valve, and otherwise, a finishing step of removing the medical liquid container, the fourth tube, and the second tube from the cylinder cartridge and connecting the third tube to the inlet tube.

* * * * *